(12) United States Patent
Nakagawa et al.

(10) Patent No.: US 9,090,524 B2
(45) Date of Patent: Jul. 28, 2015

(54) METHOD FOR MANUFACTURING HYDROCARBON

(71) Applicant: Toyoda Gosei Co., Ltd., Kiyosu-shi, Aichi-ken (JP)

(72) Inventors: Hiroyuki Nakagawa, Kiyosu (JP); Seitaro Taki, Kiyosu (JP); Hisashi Mizuno, Kiyosu (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 0 days.

(21) Appl. No.: 14/306,497

(22) Filed: Jun. 17, 2014

(65) Prior Publication Data
US 2015/0025159 A1 Jan. 22, 2015

(30) Foreign Application Priority Data

Jul. 19, 2013 (JP) ................................. 2013-150258

(51) Int. Cl.
 *C07C 27/06* (2006.01)
 *C07C 1/12* (2006.01)
 *C01B 3/04* (2006.01)
(52) U.S. Cl.
 CPC . C07C 1/12 (2013.01); C01B 3/042 (2013.01); C07C 2523/46 (2013.01); C07C 2523/745 (2013.01); C07C 2523/75 (2013.01)
(58) Field of Classification Search
 CPC ...... C07C 29/1518; C07C 31/04; C07C 1/12; C07C 29/153
 USPC .................................................. 518/702, 704
 See application file for complete search history.

(56) References Cited

U.S. PATENT DOCUMENTS 7,883,805 B2 * 2/2011 Nakai et al. ................... 429/416

FOREIGN PATENT DOCUMENTS

| JP | 08-127544 | 5/1996 |
| JP | 2000-344689 | 12/2000 |
| JP | 2004-505879 | 2/2004 |
| JP | 2008-150289 | 3/2008 |

OTHER PUBLICATIONS

Park et al, Journal of Catalysis, 2009, 266, 92-97.*
U.S. Appl. No. 14/361,709, filed May 30, 2014, Nakagawa et al.

* cited by examiner

*Primary Examiner* — Sudhakar Katakam
(74) *Attorney, Agent, or Firm* — Posz Law Group, PLC

(57) ABSTRACT

The present invention provides a method for manufacturing a hydrocarbon, the method including bringing metal Mg into contact with water and carbon dioxide and reducing the carbon dioxide. In the method, one or more elements selected from the group consisting of Group 8 elements, Group 9 elements, B, C, S, Ca, V, Mn, Ni, Ge, Zr, Nb, Pd, Ag, Sn, Pt, Au, and Ce are used as combination element(s), and the contact is effected under presence of one or more of simple substance(s) of the combination element(s), water-soluble compound(s) of the combination element(s), and ion(s) of the combination element(s).

12 Claims, 2 Drawing Sheets

METHOD FOR MANUFACTURING HYDROCARBON

TECHNICAL FIELD

The present invention relates to a method for manufacturing a hydrocarbon by reducing carbon dioxide.

BACKGROUND ART

Conventional methods for obtaining a hydrocarbon such as methane by reducing carbon dioxide include a method described in Patent Document 1 in which hydrogen gas is used as a hydrogen source under the reaction condition of a high temperature (150° C. to 400° C.) and a high pressure (1 MPa to 6 MPa). However, this method requires such a reaction condition of a high temperature and a high pressure, and thus the reaction equipment becomes complicated, leading to high cost, for example.

In contrast, as a method that is conducted under the condition of an ordinary temperature and an ordinary pressure and requires no hydrogen gas as a hydrogen source, Patent Document 2 describes a method that uses iron powder as a catalyst to obtain a hydrocarbon such as methane from carbon dioxide and water.

Although methods described in Patent Documents 3 and 4 produce hydrogen from particulate magnesium and water, these methods are not for obtaining a hydrocarbon such as methane by reducing carbon dioxide.

CITATION LIST

Patent Documents

Patent Document 1: Japanese Patent Application Publication No. 08-127544 (JP 08-127544 A)
Patent Document 2: Japanese Patent Application Publication No. 2000-344689 (JP 2000-344689 A)
Patent Document 3: Japanese Patent Application Publication No. 2008-150289 (JP 2008-150289 A)
Patent Document 4: Published Japanese Translation of PCT application No. 2004-505879 (JP-A-2004-505879)

SUMMARY OF THE INVENTION

Technical Problem

However, in the method of Patent Document 2, methane and the like cannot be obtained as much as the amount described in Patent Document 2, and the yield of the hydrocarbon (the amount of the produced hydrocarbon) is small.

For this reason, the applicant of the present invention has earlier developed a method for producing a hydrocarbon by bringing magnesium or a magnesium compound into contact with water and carbon dioxide and reducing the carbon dioxide in PCT/JP2013/050789 that had not been published at the time of filling of the subject application. In the invention of PCT/JP2013/050789, the yield of a hydrocarbon increases even under the condition of ordinary temperatures and ordinary pressures.

The present invention improves the invention of PCT/JP2013/050789 to further increase the yield of a hydrocarbon.

Solution to Problem

Elements will be expressed in symbols of elements. The present invention provides a method for manufacturing a hydrocarbon, the method including: bringing metal Mg into contact with water and carbon dioxide; and reducing the carbon dioxide. In the method, one or more elements selected from the group consisting of Group 8 elements, Group 9 elements, B, C, S, Ca, V, Mn, Ni, Ge, Zr, Nb, Pd, Sn, Pt, Au, and Ce are used as combination element(s), and the contact is effected under presence of one or more of simple substance(s) of the combination element(s), water-soluble compound(s) of the combination element(s), and ion(s) of the combination element(s).

Although the detail of the reaction of producing a hydrocarbon has not been clarified yet, the reaction of methane is considered to occur, for example, as shown in FIG. 1. Specifically, carbon dioxide ($CO_2$) brought into contact with water is diffused, and some of the carbon dioxide is dissolved in water ($H_2O$). Meanwhile, metal Mg brought into contact with water reacts with water adsorbed on the surface of the metal Mg, and while being oxidized, the metal Mg is in a transition state as magnesium oxide having hydrogen. A magnesium compound brought into contact with water also reacts with water adsorbed on the surface of the magnesium compound to generate hydrogen, and is in a transition state as the magnesium compound having hydrogen. The carbon dioxide contained in the water is then adsorbed on the magnesium in the transition state, and the carbon dioxide reacts with hydrogen to be reduced to produce methane. The produced methane ($CH_4$) is then considered to be desorbed from the magnesium.

The production of methane is facilitated by using one or more elements selected from the group consisting of Group 8 elements, Group 9 elements, B, C, S, Ca, V, Mn, Ni, Ge, Zr, Nb, Pd, Ag, Sn, Pt, Au, and Ce, as combination element(s), and effecting the contact under the presence of the simple substance(s) of the combination element(s), the water-soluble compound(s) of the combination element(s), or the ion(s) of the combination element(s). Although the reason of this facilitation has not been clarified yet, it is considered that at least Group 8 elements and Group 9 elements facilitate corrosion (oxidation) of metal Mg to increase a conversion effect into methane. The combination elements selected from Group 8 elements and Group 9 elements are thus not limited to specific elements.

The combination element(s) of Group 8 elements and Group 9 elements are preferably one or more elements selected from Fe, Co, and Ru. This is because these elements highly facilitate the production of methane, are readily obtainable, and have no trouble with toxicity and radioactive properties.

The combination element is particularly preferably Fe because Fe highly facilitates the production of methane and is inexpensive.

The specific surface area of the metal Mg is preferably 55 $cm^2/g$ to 70 $cm^2/g$.

The metal Mg, the combination element(s), the water, and the carbon dioxide that are thus brought into contact are preferably stirred with a hard bead.

Advantageous Effects of Invention

The present invention can provide a method for manufacturing a hydrocarbon with a high yield even under the condition of ordinary temperatures and ordinary pressures.

DESCRIPTION OF EMBODIMENTS

Figure 1:
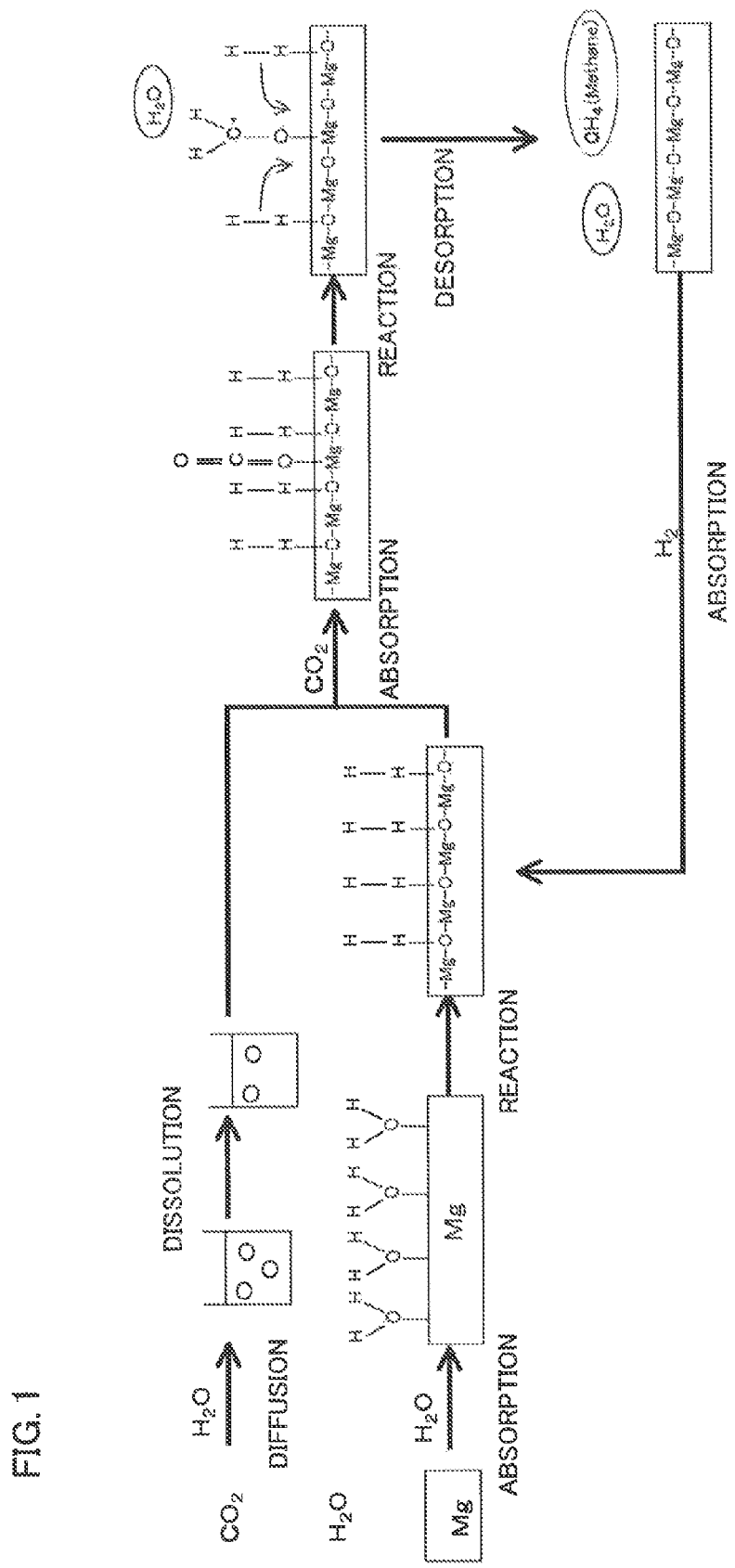
FIG. 1 is a schematic drawing of a reaction for producing methane according to an embodiment of the present invention.

The present invention provides a method for manufacturing a hydrocarbon, the method including: bringing metal Mg into contact with water and carbon dioxide; and reducing the carbon dioxide. In the method, one or more elements selected from the group consisting of Group 8 elements, Group 9 elements, B, C, S, Ca, V, Mn, Ni, Ge, Zr, Nb, Pd, Ag, Sn, Pt, Au, and Ce are used as combination element(s), and the contact is effected under the presence of the simple substance(s) of the combination element(s), the water-soluble compound(s) of the combination element(s), or the ion(s) of the combination element(s). A form of each component in the method of an embodiment of the present invention will be exemplified below.

1. Metal Mg

The form of metal Mg is not particularly limited, and the metal Mg can take the form of, for example, a particle, a sheet, a curl, a chip, and a line. The thickness of the metal Mg in a sheet form is not particularly limited, and is, for example, 0.02 to 1 mm. The size of the particulate metal Mg is not particularly limited, and is, for example, 1 to 1000 μm. The thickness of the metal Mg in a line form is not particularly limited, and is, for example, 0.1 to 1 mm. The specific surface area of the metal Mg is not particularly limited, and is, preferably, 55 to 70 $cm^2/g$ because the amount of a hydrocarbon to be produced increases.

2. Combination Element

The form of the combination element is not particularly limited, and when used as a simple substance or a water-soluble compound, the combination element can take the form of, for example, a particle, a sheet, a curl, a chip, and a line. The amount of the combination element used is not particularly limited, and when used as a simple substance or a water-soluble compound, the combination element is considered to be used preferably at a molar ratio of around 0.1 to 10 relative to the metal Mg.

3. Embodiments in which Metal Mg is Brought into Contact with Water and Carbon Dioxide The method for bringing metal Mg into contact with water and carbon dioxide is not particularly limited, and the following embodiments can be exemplified.

(1) Metal Mg is charged into water and the resultant mixture is bubbled with carbon dioxide.
(2) Metal Mg is charged into water already containing carbon dioxide.
(3) Water vapor, sprayed water, or the like is used instead of effecting the contact in water. For example, metal Mg is put into atmosphere containing carbon dioxide, and water vapor or sprayed water is brought into contact with the metal Mg.

4. Stir and Hard Beads

The metal Mg, the water, and the carbon dioxide that are thus brought into contact are preferably stirred with hard beads. This is because the metal Mg is pulverized and ground by being stirred with hard beads to cause reaction between a new surface of the metal Mg and water. If the production process is conducted in water, such stirring can reduce non-uniformity in concentration of carbon dioxide in water.

The hard beads are not particularly limited so long as Mohs hardness (the following numbers in parentheses indicate Mohs hardness in this sentence) of the beads as a material property is higher than that of metal Mg (2.5). Examples thereof include ceramic beads of zirconia (8), alumina (9), and quartz (7), and beads of agate (7), chrome steel (7.7), and SUS304 (6). The particle diameter of the hard bead is not particularly limited and is, for example, 0.1 to 10.0 mm.

5. Hydrocarbon

The hydrocarbon obtained in the production process is not particularly limited. Examples thereof include alkanes such as methane, ethane, and propane, and alkenes such as ethylene and propylene.

6. Regarding Temperatures and Pressures

In the method for manufacturing a hydrocarbon of an embodiment of the present invention, although the reaction can be performed under the atmosphere at ordinary temperatures and ordinary pressures, the reaction may also be performed under the atmosphere at temperatures and pressures other than ordinary temperatures and ordinary pressures. Two examples of temperatures and pressures other than ordinary temperatures and ordinary pressures will be explained below. Even with these examples, hydrocarbons are obtained with high yields.

(1) An example in which temperatures and pressures become other than ordinary temperatures and ordinary pressures due to a change in temperature, for example, resulting from an exothermic or endothermic reaction involved in the reaction, and a change in pressure resulting from, for example, a change in the amount of the gas in the reaction container (according to production or decomposition of the gas).
(2) An example in which temperatures and pressures become other than ordinary temperatures and ordinary pressures due to external controls for heating or cooling and for pressurizing or depressurizing.

7. Regarding Hydrogen Gas

In an embodiment of the present invention, iron or the like facilitates hydrogen generation caused by oxidation of magnesium as described above. There is thus no need to supply a hydrogen gas from the exterior, but this does not exclude the supply of a hydrogen gas from the exterior.

EXAMPLES

As shown in Table 1 below, under the presence of one combination element selected from B, C, Al, Si, S, Ca, Ti, V, Mn, Fe, Co, Ni, Cu, Zn, Ga, Ge, Zr, Nb, Ru, Pd, Ag, Sn, Pt, Au, La, and Ce (in the order of atomic number), which are considered to be readily used as combination elements in the method of an embodiment of the present invention among various elements (provided that CaO is used instead of Ca from a safety standpoint), metal Mg was brought into contact with water and carbon dioxide, the carbon dioxide was reduced to produce a hydrocarbon, and the gas of the hydrocarbon was analyzed.

The examples employing the combination elements with which the amount of the produced methane was large are designated as Examples 1 to 19 while the examples employing the combination elements with which the amount of the produced methane was small are designated as Comparative Examples 3 to 9, as compared with Comparative Example 1 in which metal Mg was brought into contact with water and carbon dioxide under the absence of a combination element. While the amount of the metal Mg was set to be equal in these examples, in an example designated as Comparative Example 2, the metal Mg whose amount was doubled was brought into contact with water and carbon dioxide under the absence of a combination element.

TABLE 1

|  |  |  | Example 1 | Example 2 | Example 3 | Example 4 | Example 5 |
|---|---|---|---|---|---|---|---|
| Mixed content | water | | 90 ml | 90 ml | 90 ml | 90 ml | 90 ml |
| | $CO_2$ | | 1 minute | 1 minute | 1 minute | 1 minute | 1 minute |
| | Mg | 371 μm | 0.2 g | 0.2 g | 0.2 g | 0.2 g | 0.2 g |
| | B | 45 μm or less | 0.2 g | | | | |
| | C | 50 μm or less | | 0.2 g | | | |
| | Al | 150 μm or less | | | | | |
| | Si | 300 μm or less | | | | | |
| | S | 75 μm or less | | | 0.2 g | | |
| | CaO | 500 μm or less | | | | 0.2 g | |
| | Ti | 250 μm or less | | | | | |
| | V | 300 μm or less | | | | | 0.2 g |
| | Mn | 300 μm or less | | | | | |
| | Fe | 36 μm | | | | | |
| | Co | 150 μm or less | | | | | |
| | Ni | 150 μm | | | | | |
| | Cu | 130 μm | | | | | |
| | Zn | 150 μm or less | | | | | |
| | Ga | 850 μm or less | | | | | |
| | Ge | 300 μm or less | | | | | |
| | Zr | 45 μm or less | | | | | |
| | Nb | 75 μm or less | | | | | |
| | Ru | 50 μm or less | | | | | |
| | Pd | 250 μm or less | | | | | |
| | Ag | 75 μm or less | | | | | |
| | Sn | 45 μm or less | | | | | |
| | Pt | 75 μm or less | | | | | |
| | Au | 150 μm or less | | | | | |
| | La | 850 μm or less | | | | | |
| | Ce | 850 μm or less | | | | | |
| Reaction Condition | | Place | Indoor | Indoor | Indoor | Indoor | Indoor |
| | | Reaction Time | 1 day | 1 day | 1 day | 1 day | 1 day |
| | | Stir | Performed | Performed | Performed | Performed | Performed |
| | | Zirconia Beads | Present | Present | Present | Present | Present |
| Amount of produced gas | | Methane (ppm) | 5140 | 4831 | 5352 | 4566 | 5221 |
| | | CO (ppm) | 7 | 441 | 21 | 4 | 19 |

|  |  |  | Example 6 | Example 7 | Example 8 | Example 9 | Example 10 |
|---|---|---|---|---|---|---|---|
| Mixed content | water | | 90 ml | 90 ml | 90 ml | 90 ml | 90 ml |
| | $CO_2$ | | 1 minute | 1 minute | 1 minute | 1 minute | 1 minute |
| | Mg | 371 μm | 0.2 g | 0.2 g | 0.2 g | 0.2 g | 0.2 g |
| | B | 45 μm or less | | | | | |
| | C | 50 μm or less | | | | | |
| | Al | 150 μm or less | | | | | |
| | Si | 300 μm or less | | | | | |
| | S | 75 μm or less | | | | | |
| | CaO | 500 μm or less | | | | | |
| | Ti | 250 μm or less | | | | | |
| | V | 300 μm or less | | | | | |
| | Mn | 300 μm or less | 0.2 g | | | | |
| | Fe | 36 μm | | 0.2 g | | | |
| | Co | 150 μm or less | | | 0.2 g | | |
| | Ni | 150 μm | | | | 0.2 g | |
| | Cu | 130 μm | | | | | |
| | Zn | 150 μm or less | | | | | |
| | Ga | 850 μm or less | | | | | |
| | Ge | 300 μm or less | | | | | 0.2 g |
| | Zr | 45 μm or less | | | | | |
| | Nb | 75 μm or less | | | | | |
| | Ru | 50 μm or less | | | | | |
| | Pd | 250 μm or less | | | | | |
| | Ag | 75 μm or less | | | | | |
| | Sn | 45 μm or less | | | | | |
| | Pt | 75 μm or less | | | | | |
| | Au | 150 μm or less | | | | | |
| | La | 850 μm or less | | | | | |
| | Ce | 850 μm or less | | | | | |
| Reaction Condition | | Place | Indoor | Indoor | Indoor | Indoor | Indoor |
| | | Reaction Time | 1 day | 1 day | 1 day | 1 day | 1 day |
| | | Stir | Performed | Performed | Performed | Performed | Performed |
| | | Zirconia Beads | Present | Present | Present | Present | Present |
| Amount of produced gas | | Methane (ppm) | 3997 | 8964 | 8729 | 5948 | 4428 |
| | | CO (ppm) | 10 | 2 | 2 | 4 | 37 |

TABLE 1-continued

|  |  |  | Example 11 | Example 12 | Example 13 | Example 14 | Example 15 |
|---|---|---|---|---|---|---|---|
| Mixed content | water | | 90 ml | 90 ml | 90 ml | 90 ml | 90 ml |
| | CO₂ | | 1 minute | 1 minute | 1 minute | 1 minute | 1 minute |
| | Mg | 371 μm | 0.2 g | 0.2 g | 0.2 g | 0.2 g | 0.2 g |
| | B | 45 μm or less | | | | | |
| | C | 50 μm or less | | | | | |
| | Al | 150 μm or less | | | | | |
| | Si | 300 μm or less | | | | | |
| | S | 75 μm or less | | | | | |
| | CaO | 500 μm or less | | | | | |
| | Ti | 250 μm or less | | | | | |
| | V | 300 μm or less | | | | | |
| | Mn | 300 μm or less | | | | | |
| | Fe | 36 μm | | | | | |
| | Co | 150 μm or less | | | | | |
| | Ni | 150 μm | | | | | |
| | Cu | 130 μm | | | | | |
| | Zn | 150 μm or less | | | | | |
| | Ga | 850 μm or less | | | | | |
| | Ge | 300 μm or less | | | | | |
| | Zr | 45 μm or less | 0.2 g | | | | |
| | Nb | 75 μm or less | | 0.2 g | | | |
| | Ru | 50 μm or less | | | 0.2 g | | |
| | Pd | 250 μm or less | | | | 0.2 g | |
| | Ag | 75 μm or less | | | | | 0.2 g |
| | Sn | 45 μm or less | | | | | |
| | Pt | 75 μm or less | | | | | |
| | Au | 150 μm or less | | | | | |
| | La | 850 μm or less | | | | | |
| | Ce | 850 μm or less | | | | | |
| Reaction Condition | | Place | Indoor | Indoor | Indoor | Indoor | Indoor |
| | | Reaction Time | 1 day | 1 day | 1 day | 1 day | 1 day |
| | | Stir | Performed | Performed | Performed | Performed | Performed |
| | | Zirconia Beads | Present | Present | Present | Present | Present |
| Amount of produced gas | | Methane (ppm) | 7639 | 4286 | 9769 | 5294 | 4689 |
| | | CO (ppm) | 33 | 7 | 3 | 1 | 6 |

|  |  |  | Example 16 | Example 17 | Example 18 | Example 19 |
|---|---|---|---|---|---|---|
| Mixed content | water | | 90 ml | 90 ml | 90 ml | 90 ml |
| | CO₂ | | 1 minute | 1 minute | 1 minute | 1 minute |
| | Mg | 371 μm | 0.2 g | 0.2 g | 0.2 g | 0.2 g |
| | B | 45 μm or less | | | | |
| | C | 50 μm or less | | | | |
| | Al | 150 μm or less | | | | |
| | Si | 300 μm or less | | | | |
| | S | 75 μm or less | | | | |
| | CaO | 500 μm or less | | | | |
| | Ti | 250 μm or less | | | | |
| | V | 300 μm or less | | | | |
| | Mn | 300 μm or less | | | | |
| | Fe | 36 μm | | | | |
| | Co | 150 μm or less | | | | |
| | Ni | 150 μm | | | | |
| | Cu | 130 μm | | | | |
| | Zn | 150 μm or less | | | | |
| | Ga | 850 μm or less | | | | |
| | Ge | 300 μm or less | | | | |
| | Zr | 45 μm or less | | | | |
| | Nb | 75 μm or less | | | | |
| | Ru | 50 μm or less | | | | |
| | Pd | 250 μm or less | | | | |
| | Ag | 75 μm or less | | | | |
| | Sn | 45 μm or less | 0.2 g | | | |
| | Pt | 75 μm or less | | 0.2 g | | |
| | Au | 150 μm or less | | | 0.2 g | |
| | La | 850 μm or less | | | | |
| | Ce | 850 μm or less | | | | 0.2 g |
| Reaction Condition | | Place | Indoor | Indoor | Indoor | Indoor |
| | | Reaction Time | 1 day | 1 day | 1 day | 1 day |
| | | Stir | Performed | Performed | Performed | Performed |
| | | Zirconia Beads | Present | Present | Present | Present |
| Amount of produced gas | | Methane (ppm) | 5508 | 5901 | 7503 | 3801 |
| | | CO (ppm) | 30 | 1 | 1 | 4 |

TABLE 1-continued

|  |  | Comparative Example 1 | Comparative Example 2 | Comparative Example 3 | Comparative Example 4 | Comparative Example 5 |
|---|---|---|---|---|---|---|
| Mixed content | water | 90 ml | 90 ml | 90 ml | 90 ml | 90 ml |
|  | $CO_2$ | 1 minute | 1 minute | 1 minute | 1 minute | 1 minute |
|  | Mg 371 μm | 0.2 g | 0.4 g | 0.2 g | 0.2 g | 0.2 g |
|  | B 45 μm or less |  |  |  |  |  |
|  | C 50 μm or less |  |  |  |  |  |
|  | Al 150 μm or less |  |  | 0.2 g |  |  |
|  | Si 300 μm or less |  |  |  | 0.2 g |  |
|  | S 75 μm or less |  |  |  |  |  |
|  | CaO 500 μm or less |  |  |  |  |  |
|  | Ti 250 μm or less |  |  |  |  | 0.2 g |
|  | V 300 μm or less |  |  |  |  |  |
|  | Mn 300 μm or less |  |  |  |  |  |
|  | Fe 36 μm |  |  |  |  |  |
|  | Co 150 μm or less |  |  |  |  |  |
|  | Ni 150 μm |  |  |  |  |  |
|  | Cu 130 μm |  |  |  |  |  |
|  | Zn 150 μm or less |  |  |  |  |  |
|  | Ga 850 μm or less |  |  |  |  |  |
|  | Ge 300 μm or less |  |  |  |  |  |
|  | Zr 45 μm or less |  |  |  |  |  |
|  | Nb 75 μm or less |  |  |  |  |  |
|  | Ru 50 μm or less |  |  |  |  |  |
|  | Pd 250 μm or less |  |  |  |  |  |
|  | Ag 75 μm or less |  |  |  |  |  |
|  | Sn 45 μm or less |  |  |  |  |  |
|  | Pt 75 μm or less |  |  |  |  |  |
|  | Au 150 μm or less |  |  |  |  |  |
|  | La 850 μm or less |  |  |  |  |  |
|  | Ce 850 μm or less |  |  |  |  |  |
| Reaction Condition | Place | Indoor | Indoor | Indoor | Indoor | Indoor |
|  | Reaction Time | 1 day | 1 day | 1 day | 1 day | 1 day |
|  | Stir | Performed | Performed | Performed | Performed | Performed |
|  | Zirconia Beads | Present | Present | Present | Present | Present |
| Amount of produced gas | Methane (ppm) | 3583 | 4776 | 758 | 1061 | 2426 |
|  | CO (ppm) | 4 | 4 | 8 | 8 | 32 |

|  |  | Comparative Example 6 | Comparative Example 7 | Comparative Example 8 | Comparative Example 9 |
|---|---|---|---|---|---|
| Mixed content | water | 90 ml | 90 ml | 90 ml | 90 ml |
|  | $CO_2$ | 1 minute | 1 minute | 1 minute | 1 minute |
|  | Mg 371 μm | 0.2 g | 0.2 g | 0.2 g | 0.2 g |
|  | B 45 μm or less |  |  |  |  |
|  | C 50 μm or less |  |  |  |  |
|  | Al 150 μm or less |  |  |  |  |
|  | Si 300 μm or less |  |  |  |  |
|  | S 75 μm or less |  |  |  |  |
|  | CaO 500 μm or less |  |  |  |  |
|  | Ti 250 μm or less |  |  |  |  |
|  | V 300 μm or less |  |  |  |  |
|  | Mn 300 μm or less |  |  |  |  |
|  | Fe 36 μm |  |  |  |  |
|  | Co 150 μm or less |  |  |  |  |
|  | Ni 150 μm |  |  |  |  |
|  | Cu 130 μm | 0.2 g |  |  |  |
|  | Zn 150 μm or less |  | 0.2 g |  |  |
|  | Ga 850 μm or less |  |  | 0.2 g |  |
|  | Ge 300 μm or less |  |  |  |  |
|  | Zr 45 μm or less |  |  |  |  |
|  | Nb 75 μm or less |  |  |  |  |
|  | Ru 50 μm or less |  |  |  |  |
|  | Pd 250 μm or less |  |  |  |  |
|  | Ag 75 μm or less |  |  |  |  |
|  | Sn 45 μm or less |  |  |  |  |
|  | Pt 75 μm or less |  |  |  |  |
|  | Au 150 μm or less |  |  |  |  |
|  | La 850 μm or less |  |  |  | 0.2 g |
|  | Ce 850 μm or less |  |  |  |  |
| Reaction Condition | Place | Indoor | Indoor | Indoor | Indoor |
|  | Reaction Time | 1 day | 1 day | 1 day | 1 day |
|  | Stir | Performed | Performed | Performed | Performed |
|  | Zirconia Beads | Present | Present | Present | Present |
| Amount of produced gas | Methane (ppm) | 1947 | 1987 | 2259 | 3344 |
|  | CO (ppm) | 8 | 583 | 42 | 5 |

The particles of commercially available pure simple substances were used as metal Mg, B, C, Al, Si, S, Ti, V, Mn, Fe, Co, Ni, Cu, Zn, Ga, Ge, Zr, Nb, Ru, Pd, Ag, Sn, Pt, Au, La, and Ce. Specifically, the metal Mg and V were manufactured by NACALAI TESQUE, INC.; B, C, Mn, Fe, Zn, Ga, Ge, Zr, Nb, Ru, Pd, Ag, Pt, La, and Ce were manufactured by Wako Pure Chemical Industries, Ltd.; Al, Si, and S were manufactured by KOJUNDO CHEMICAL LABORATORY CO., LTD; Ti, Ni, Cu, and Sn were manufactured by FUKUDA METAL FOIL & POWDER Co., LTD.; Co was manufactured by KISHIDA CHEMICAL Co., Ltd.; and Au was manufactured by COSMO BIO CO., LTD. CaO was also manufactured by Wako Pure Chemical Industries, Ltd. Table 1 shows the sizes of the particles of the substances. The size of each of the particles of the metal Mg and Fe was the average of the sizes of 20 particles (the maximum diameter of each particle) measured using a stereomicroscope or a scanning electron microscope (SEM). The size of each of the particles of the combination elements except for the metal Mg and Fe indicates the description in each of the commercial items.

Zirconia beads used were manufactured by Saint-Gobain K.K. (having a commercially available particle diameter of 0.5 mm).

As a reaction container, a vial made of colorless and transparent glass (a volume of 150 mL, a diameter of 50 mm, and a height of 95 mm) was used. The vial was plugged with a cap composed of an outer cap made of resin and having a hole in its central part and an inner cap made of rubber. By piercing a syringe needle into the inner cap, gas can be collected from a head space inside the vial. The vial was fixed on a metal plate (a stainless steel plate having a thickness of 3 mm) to prevent seal leakage.

Gas components were analyzed by gas chromatography (100HC, manufactured by NEW COSMOS ELECTRIC CO., LTD.).

Reactions in the examples were performed as described below. In each of the examples, all steps were performed under the atmosphere at ordinary temperatures and ordinary pressures without performing external controls for heating or cooling and for pressurizing or depressurizing. The ordinary temperatures are, for example, 20° C.±15° C. (5° C. to 35° C.). The ordinary pressures are, for example, 0.1 MPa±0.05 MPa (0.05 MPa to 0.15 MPa).

To a vial, 30 g of zirconia beads was added, and then 90 mL of water (pure water) was added.

To the resultant vial, 0.2 g of particles of metal Mg and 0.2 g of particles of a combination element were added. However, 0.2 g of particles of metal Mg alone was added in Comparative Example 1, and 0.4 g of particles of metal Mg alone was added in Comparative Example 2.

Next, through a tube inserted into the opening of the vial, carbon dioxide was infused in water near the bottom in the vial for 1 minute (a flow rate of 0.8 L/min) for bubbling. After that, the tube was removed from the vial, and then the vial was sealed with a cap.

A reaction was performed while the vial was vertically shaken indoors (the inside of a room whose temperature had been adjusted to around 23° C.) with a shaker (a frequency of shaking of 10 times/sec) for 1 day. After the reaction, gas was collected from a head space inside the vial using a syringe, and components of the gas were analyzed.

The amount of the produced methane was large in the examples in which metal Mg was brought into contact with water and carbon dioxide under the presence of B, C, S, Ca, V, Mn, Fe, Co, Ni, Ge, Zr, Nb, Ru, Pd, Ag, Sn, Pt, Au, or Ce (combination element), as compared with Comparative Example 1 in which an equivalent amount of metal Mg was brought into contact with water and carbon dioxide under the absence of a combination element. These examples were designated as Examples 1 to 19 as described above.

In contrast, the amount of the produced methane was small in the examples in which metal Mg was brought into contact with water and carbon dioxide under the presence of Al, Si, Ti, Cu, Zn, Ga, or La (combination element) as compared with Comparative Example 1 in which an equivalent amount of metal Mg was brought into contact with water and carbon dioxide under the absence of a combination element. These examples were designated as Comparative Examples 3 to 9 as described above.

The results in Examples 1 to 19 indicate that methanation of carbon dioxide was facilitated by the use of a simple substance of any one of B, C, S, Ca, V, Mn, Fe, Co, Ni, Ge, Zr, Nb, Ru, Pd, Ag, Sn, Pt, Au, and Ce or a water-soluble compound (CaO) as a combination element. It can be considered from the results that methanation of carbon dioxide is facilitated also when two or more combination elements selected from B, C, S, Ca, V, Mn, Fe, Co, Ni, Ge, Zr, Nb, Ru, Pd, Ag, Sn, Pt, Au, and Ce are used.

It can be evaluated from the description of the above that, in each of Examples 1 to 19, the hydrocarbon was obtained with a high yield under the condition of ordinary temperatures and ordinary pressures as compared with the case using metal Mg alone. Accordingly, external controls for heating or cooling and for pressurizing or depressurizing are not necessarily required to obtain a given amount of a hydrocarbon, and thus, reaction equipment can be simplified to lower the costs in a practical use, for example. Furthermore, because inexpensive water is used as a hydrogen source instead of an expensive hydrogen gas, methane can be synthesized with a lower cost.

First Modification

A modification using the ions of a combination element has been investigated instead of using the simple substance or the water-soluble compound of a combination element as in Examples 1 to 19. Specifically, the modification of Example 7 was performed in the following manner.

To a vial, 30 g of zirconia beads was added, and then 90 mL of water (pure water) was added, followed by adding 0.2 g of particles of Fe identical with Fe in Example 7 (adding no Mg).

Next, through a tube inserted into the opening of the vial, carbon dioxide was infused in water near the bottom in the vial for 1 minute (a flow rate of 0.8 L/min) for bubbling. After that, the tube was removed from the vial, and then the vial was sealed with a cap.

The vial was vertically shaken indoors (the inside of a room whose temperature had been adjusted to around 23° C.) with a shaker (a frequency of shaking of 10 times/sec) for 1 day.

After the completion of the shaking, the water in the vial was subjected to suction filtration. The resultant filtrate was centrifuged at 10,000 rpm for 10 minutes to obtain 75 mL of the supernatant liquid. The Fe concentration of the supernatant liquid was measured by atomic absorption spectrophotometry and was found to be 5 mg/L. Pure water was added to the supernatant liquid to be 90 mL. The resultant liquid is called "Fe ion water", hereinafter.

To a vial, 30 g of zirconia beads was added again, and then 90 mL of the Fe ion water was added, followed by adding 0.2 g of particles of metal Mg identical with the metal Mg in Example 7.

Next, through a tube inserted into the opening of the vial, carbon dioxide was infused in the Fe ion water near the bottom in the vial for 1 minute (a flow rate of 0.8 L/min) for bubbling. After that, the tube was removed from the vial, and then the vial was sealed with a cap.

A reaction was performed while the vial was vertically shaken indoors (the inside of a room whose temperature had been adjusted to around 23° C.) with a shaker (a frequency of shaking of 10 times/sec) for 1 day. After the reaction, gas was collected from a head space inside the vial using a syringe, and components of the gas were analyzed.

In the present modification, the amount of produced methane was 8,534 ppm, which was almost equal to that of 8,964 ppm in Example 7 and was obviously larger than that in Comparative Example 1. This result indicates that methanation of carbon dioxide was facilitated also when metal Mg was brought into contact with water and carbon dioxide under the presence of the ions of a combination element, in a similar manner to the case under the presence of the simple substance or the water-soluble compound of a combination element.

Second Modification

The following shows examination of influence of the shape of metal Mg on the amount of methane to be produced by employing metal Mg having shapes except a particulate shape, specifically, metal Mg in the form of a sheet, a curl, or a chip whose size and specific surface area are indicated in Table 2. First, this experiment was performed under the absence of a combination element. Specifically, the second modification was performed under the same condition as Comparative Example 1 except that the particulate metal Mg in Comparative Example 1 was changed to metal Mg in the form of a sheet, a curl, or a chip in Table 2.

TABLE 2

| Shape of Mg | Size | Specific surface area | | | | Amount of produced Methane |
|---|---|---|---|---|---|---|
| | | Surface area a [cm$^2$] | Volume b [cm$^3$] | Density c [g/cm$^3$] | Specific surface area a/(bc) [cm$^2$/g] | |
| Particle | Diameter: 371 μm | 0.004321927 | 2.67239E−05 | 1.738 | 93 | 4776 ppm |
| Sheet | Thickness: 0.27 mm Width: 10 mm Length: 5 mm | 1.081 | 0.0135 | 1.738 | 46 | 5340 ppm |
| Curl | Thickness: 0.35 mm Width: 3 mm Length: 5 mm | 0.356 | 0.00525 | 1.738 | 39 | 6176 ppm |
| Chip | Thickness: 0.30 mm Width: 0.6 mm Length: 3 mm | 0.0576 | 0.00054 | 1.738 | 61 | 8135 ppm |

Figure 2:
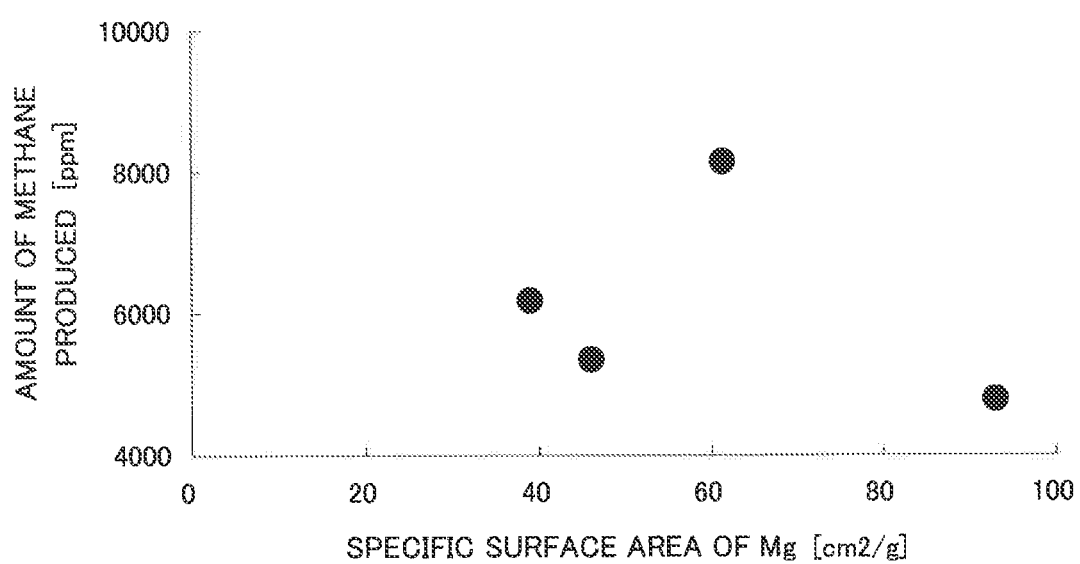
FIG. 2 is a graph illustrating a relation between the specific surface area of metal Mg and the methane yield.

Table 2 and FIG. 2 show a comparison between the amount of the methane produced using the metal Mg in the forms of a sheet, a curl, and a chip and the amount of the methane produced using the particulate metal Mg. The amount of methane produced was highest when the metal Mg in the form of a chip having a specific surface area of 61 cm$^2$/g was used. This result was considered to be the same with the case where a combination element was used, and thus, an experiment was performed under the presence of a combination element as follows. Specifically, the experiment was performed under the same condition as Example 7 employing Fe as a combination element except that the particulate metal Mg in Example 7 was changed to metal Mg in the form of a chip in Table 2. The amount of the methane thus produced was 11,186 ppm, which was larger than the case where the particulate metal Mg was used. It is considered from this result that Mg having a specific surface area of around 55 cm$^2$/g to 70 cm$^2$/g is preferably used in order to increase the amount of methane to be produced.

Note that the present invention is not limited to the above examples, and changes and modifications can be suitably made for reduction to practice, without departing from the gist of the present invention.

The invention claimed is:

1. A method for manufacturing a hydrocarbon, the method comprising:
   bringing metallic Mg into contact with liquid water and carbon dioxide; and
   reducing the carbon dioxide, wherein
   the contact of the metallic Mg with the liquid water and carbon dioxide is effected under presence of at least one combination element selected from the group consisting of Group 8 elements, Group 9 elements, B, C, S, Ca, V, Mn, Ni, Ge, Zr, Nb, Pd, Ag, Sn, Pt, Au, Ce, a water-soluble compound thereof, and an ion thereof.

2. The method for manufacturing a hydrocarbon according to claim 1, wherein the combination element includes an element selected from the group consisting of Fe, Co, and Ru.

3. The method for manufacturing a hydrocarbon according to claim 2, wherein the combination element is Fe.

4. The method for manufacturing a hydrocarbon according to claim 1, wherein a specific surface area of the metallic Mg is 55 cm$^2$/g to 70 cm$^2$/g.

5. The method for manufacturing a hydrocarbon according to claim 1, wherein the metallic Mg, the liquid water, the carbon dioxide, and the at least one combination element are all brought into contact by stirring with a hard bead.

6. The method for manufacturing a hydrocarbon according to claim 1, wherein all steps are carried out at ordinary temperatures of 5° C. to 35° C. and, ordinary pressures of 0.05 MPa to 0.15 MPa.

7. The method for manufacturing a hydrocarbon according to claim 1 wherein the liquid water forms a layer of liquid water on the surface of the metallic Mg and the carbon dioxide contacts the layer of liquid water formed on the surface of the metallic Mg.

8. The method for manufacturing a hydrocarbon according to claim 4, wherein the at least one combination element is present in an amount corresponding to a molar ratio of about 0.1 to 10 relative to an amount of the metallic Mg.

9. A method for manufacturing a hydrocarbon, the method comprising:
   contacting a surface area of metallic Mg with liquid water; and
   contacting the surface of metallic Mg with carbon dioxide at the same time the surface of the metallic Mg is in contact with the liquid water; and
   reducing the carbon dioxide to form a hydrocarbon,
   wherein the contacting of the surface of metallic Mg by the liquid water and the carbon dioxide is carried out in a presence of an effective amount of at least one combination element for increasing production of the hydrocarbon, and the combination element is selected from the group consisting of Group 8 elements, Group 9 elements, B, C, S, Ca, V, Mn, Ni, Ge, Zr, Nb, Pd, Ag, Sn, Pt, Au, Ce, a water-soluble compound thereof, an ion thereof.

10. The method for manufacturing a hydrocarbon according to claim 9, wherein the metallic Mg has a surface area of 55 $cm^2/g$ to 70 $cm^2/g$, and the at least one combination element is present in an amount corresponding to a molar ratio of 0.1 to 10 relative to an amount of metallic Mg.

11. A method for manufacturing a hydrocarbon, the method comprising:
performing steps as follows in a presence of at least one combination element effective for increasing production of a hydrocarbon:
adsorbing water on the surface of metallic Mg, and generating hydrogen; and
contacting carbon dioxide with the hydrogen generated on the surface of metallic Mg, and reducing the carbon dioxide to a hydrocarbon,
wherein the combination element is selected from the group consisting of Group 8 elements, Group 9 elements, B, C, S, Ca, V, Mn, Ni, Ge, Zr, Nb, Ag, Sn, Pt, Au, Ce, a water-soluble compound thereof, and an ion thereof.

12. The method for manufacturing a hydrocarbon according to claim 11, wherein the metallic Mg has a surface area of 55 $cm^2/g$ to 70 $cm^2/g$, and the at least one combination element is present in an amount corresponding to a molar ratio of about 0.1 to 10 relative to the amount of metallic Mg.

* * * * *